US008993963B2

(12) United States Patent
von Harrach et al.

(10) Patent No.: US 8,993,963 B2
(45) Date of Patent: Mar. 31, 2015

(54) MOUNTING STRUCTURES FOR MULTI-DETECTOR ELECTRON MICROSCOPES

(71) Applicant: FEI Company, Hillsboro, OR (US)

(72) Inventors: Hanno Sebastian von Harrach, Eindhoven (NL); Bert Henning Freitag, Eindhoven (NL); Pleun Dona, Veldhoven (NL)

(73) Assignee: FEI Company, Hillsboro, OR (US)

(*) Notice: Subject to any disclaimer, the term of this patent is extended or adjusted under 35 U.S.C. 154(b) by 0 days.

(21) Appl. No.: 14/325,166

(22) Filed: Jul. 7, 2014

(65) Prior Publication Data

US 2014/0319347 A1 Oct. 30, 2014

Related U.S. Application Data

(60) Division of application No. 14/090,855, filed on Nov. 26, 2013, now abandoned, which is a continuation of application No. 13/855,373, filed on Apr. 2, 2013, now Pat. No. 8,592,764, which is a continuation of (Continued)

(51) Int. Cl.
*H01J 37/244* (2006.01)
*H01J 37/26* (2006.01)
(Continued)

(52) U.S. Cl.
CPC ............... *H01J 37/244* (2013.01); *H01J 37/26* (2013.01); *H01J 37/28* (2013.01); *H01J 2237/002* (2013.01); *H01J 2237/2442* (2013.01);

(Continued)

(58) Field of Classification Search
USPC ............................ 250/307, 310, 311, 370.15
See application file for complete search history.

(56) References Cited

U.S. PATENT DOCUMENTS 3,924,126 A * 12/1975 Anderson et al. ............ 250/311
4,833,698 A 5/1989 Flannery et al.

(Continued)

FOREIGN PATENT DOCUMENTS

JP 07014538 1/1995
JP 08222172 8/1996

(Continued)

OTHER PUBLICATIONS

Fiorini, C., et al., "A new detection system for x-ray microanalysis based on a silicon drift detector with Peltier cooling," Rev. Sci. Instrum., Jun. 1997, pp. 2461-2465, vol. 68, No. 6.

(Continued)

*Primary Examiner* — David A Vanore
(74) *Attorney, Agent, or Firm* — Scheinberg & Associates, PC; Michael O. Scheinberg

(57) ABSTRACT

A detector support for an electron microscope including a detector support ring and flexible elements, wherein a first end of each of the flexible elements is connected to the support ring, and wherein the detector support ring and the flexible elements are configured to support at least two detectors in a circumferential arrangement around an optical axis of the electron microscope such that an optical axis of each of the at least two detectors intersects the optical axis of the electron microscope and a target point of the at least two detectors is maintained relatively constant over a temperature change.

21 Claims, 5 Drawing Sheets

Related U.S. Application Data application No. 13/312,689, filed on Dec. 6, 2011, now Pat. No. 8,410,439, which is a continuation of application No. 12/494,227, filed on Jun. 29, 2009, now Pat. No. 8,080,791.

(60) Provisional application No. 61/122,295, filed on Dec. 12, 2008.

(51) Int. Cl.
*H01J 49/06* (2006.01)
*H01J 37/28* (2006.01)
*G01N 23/225* (2006.01)

(52) U.S. Cl.
CPC ...... *H01J2237/28* (2013.01); *H01J 2237/2802* (2013.01); *G01N 23/225* (2013.01)
USPC ....... 250/311; 250/307; 250/310; 250/370.15

(56) References Cited

U.S. PATENT DOCUMENTS 4,910,399 A * 3/1990 Taira et al. .................... 250/310
4,931,650 A * 6/1990 Lowe et al. ................... 250/397
5,075,555 A * 12/1991 Woldseth et al. ........ 250/370.15
5,199,054 A 3/1993 Adams et al.
5,266,802 A * 11/1993 Kasai ............................ 250/310
5,274,237 A * 12/1993 Gallagher et al. ....... 250/370.15
5,298,747 A 3/1994 Ichikawa et al.
5,317,154 A 5/1994 Honda
5,497,008 A 3/1996 Kumakhov
5,569,925 A 10/1996 Quinn et al.
5,602,894 A 2/1997 Bardash
5,682,415 A 10/1997 O'Hara
5,703,923 A 12/1997 Bardash
5,903,004 A 5/1999 Koshihara et al.
6,140,643 A 10/2000 Brown et al.
6,269,144 B1 7/2001 Dube et al.
6,479,818 B1 11/2002 McCarthy et al.
6,552,340 B1 * 4/2003 Krivanek et al. .................. 850/7
6,664,552 B2 * 12/2003 Shichi et al. ............. 250/492.21
6,710,341 B2 3/2004 Terauchi
7,209,545 B2 * 4/2007 Radley et al. ................. 378/137
7,294,834 B2 * 11/2007 Khursheed .................... 250/310
7,321,118 B2 * 1/2008 Ward ............................ 250/309
7,378,664 B1 * 5/2008 Howard et al. .......... 250/370.15
7,382,856 B2 6/2008 Radley et al.
7,498,573 B2 3/2009 Kaneyama et al.
7,515,684 B2 4/2009 Gibson et al.
7,519,159 B2 * 4/2009 Radley et al. ................. 378/141
7,579,591 B2 8/2009 Takakura
7,586,093 B2 * 9/2009 Feuerbaum ................... 250/311
7,592,591 B2 9/2009 Notoya
7,684,545 B2 * 3/2010 Damento et al. .............. 378/161
7,796,726 B1 9/2010 Gendreau et al.
7,825,378 B2 11/2010 Yakushevska et al.
7,825,386 B2 11/2010 Liu et al.
7,858,946 B2 12/2010 Rohde
7,860,217 B2 12/2010 Ozawa et al.
7,989,778 B2 8/2011 Oetelaar et al.
8,080,791 B2 12/2011 von Harrach et al.
8,149,988 B2 4/2012 Bertozzi et al.
8,164,060 B2 4/2012 Liu et al.
8,389,936 B2 3/2013 Freitag et al.
8,391,581 B2 3/2013 Masuda et al.
8,410,439 B2 4/2013 von Harrach et al.
8,476,589 B2 7/2013 Benner et al.
8,581,188 B2 * 11/2013 Barbi et al. ................... 250/307
8,592,764 B2 11/2013 von Harrach et al.
2004/0061067 A1 * 4/2004 Clauss ................... 250/396 ML
2006/0097191 A1 * 5/2006 Mizuno ...................... 250/492.2
2007/0140420 A1 * 6/2007 Radley et al. ................... 378/45
2008/0029698 A1 2/2008 Kaneyama et al.
2008/0067379 A1 3/2008 Notoya
2008/0210863 A1 * 9/2008 Pinna et al. ................... 250/305
2008/0217543 A1 9/2008 Rohde
2009/0039285 A1 * 2/2009 Cooper .................... 250/442.11
2009/0133167 A1 * 5/2009 Yakushevska et al. ........... 850/3
2010/0108882 A1 * 5/2010 Zewail .......................... 250/307
2010/0108907 A1 * 5/2010 Oetelaar et al. .......... 250/441.11
2010/0148064 A1 * 6/2010 Harrach et al. ............... 250/307
2011/0006208 A1 * 1/2011 Freitag et al. ................. 250/307
2012/0049061 A1 * 3/2012 Luecken et al. .............. 250/307
2012/0112068 A1 * 5/2012 Maeda et al. ................. 250/310
2012/0273679 A1 11/2012 Bewick et al.
2014/0319347 A1 * 10/2014 von Harrach et al. ........ 250/311

FOREIGN PATENT DOCUMENTS

JP H09-119907 6/1997
JP 2003-217497 7/2003

OTHER PUBLICATIONS

Fiorini, C., et al., "Semiconductor drift detectors for X- and gamma-ray spectroscopy and imaging," Nuclear Instruments, Methods in Physics Research B, Mar. 6, 2008, pp. 2173-2181, vol. 266.

Furuya, Kazuo, et al.,"Practical Performance of Energy-Dispersive X-Ray Spectroscopy with a High-Voltage TEM up to 1,000 kV," J. Electron Microsc., 1996, pp. 285-290, vol. 45, No. 4.

Kotula, P.G., et al., "Results from two four-channel Si-drift detectors on an SEM: Conventional and annular geometries," Microsc. Microanal, 2008, pp. 1390-1391, vol. 14, Suppl. 2.

Terborg, R., et al., "New developments in state of the art silicon drift detectors (SDD) and multiple element SDD," Instrumentation and Methods, 2008, pp. 633-634, vol. 1.

Watanabe, M., et al., "The effect of large solid angles of collection on quantitative X-ray microanalysis in the AEM," Journal of Microscopy, Jul. 1999, pp. 34-43, vol. 195.

Wikipedia, "X-Ray," The Free Encyclopedia, retrieved Nov. 24, 2008, http://en.wikipedia.org/w/index.php?title=X-ray&oldid=314387999.

* cited by examiner

MOUNTING STRUCTURES FOR MULTI-DETECTOR ELECTRON MICROSCOPES

This application is a Divisional Application of U.S. application Ser. No. 14/090,855 filed Nov. 26, 2013, which is a Continuation Application of U.S. application Ser. No. 13/855,373, filed Apr. 2, 2013, now U.S. Pat. No. 8,592,764, which is a Continuation Application of U.S. application Ser. No. 13/312,689, filed Dec. 6, 2011, now U.S. Pat. No. 8,410, 439, which is a Continuation Application of U.S. application Ser. No. 12/494,227, filed Jun. 29, 2009, now U.S. Pat. No. 8,080,791, which claims priority from U.S. Provisional App. No. 61/122,295, filed Dec. 12, 2008, all of which are hereby incorporated by reference.

TECHNICAL FIELD OF THE INVENTION

The present invention relates to x-ray detectors, and in particular, to an x-ray detector for an electron microscope.

BACKGROUND OF THE INVENTION

Electron probe microanalyzers and electron microscopes having an attached x-ray spectrometer are used to determine the composition of microscopic or nanoscopic regions of a surface. The detectors determine the energy or wavelengths of x-rays emitted from the sample and infer the composition of material under the electron beam from the energy or wavelength of the x-rays. Detectors that use a crystal to disperse and analyze x-rays of different wavelengths are referred to as wavelength dispersive spectrometers (WDS) and detectors that measure the energy of incoming x-rays are referred to as energy dispersive spectrometers (EDS). While a WDS can provide better resolution and faster counting for a particular wavelength of x-ray, an EDS is better adapted to measuring x-rays of different energies from multiple elements.

Two types of semiconductor energy dispersive x-ray detectors are commonly used in electron microscopy: lithium-drifted silicon detectors "Si(Li)" and silicon drift detectors "SDD". Si(Li) detectors typically require cooling to liquid nitrogen temperatures and normally have a standardized active detection of area of 10, 30 and 50 $mm^2$. SDDs can operate at a higher temperature and can provide better resolution at high count rates. To avoid ice formation and contamination on the detector, as well as damage from backscattered electrons, a window of a light element such as berrylium is often attached in front of the detector to stop the electrons. A magnetic field can also be used near the detector entrance to divert electrons away from the detector. A collimator is often used in front of the detector to reduce x-rays from sources other than the sample from entering the detector. Some detectors, such as the one described in U.S. Pat. No. 5,569,925 to Quinn et al., include a shutter in front of the detector. When the electron microscope is operated under conditions that would generate high energy x-rays and electrons that could damage the detector, the shutter can be closed to protect the crystal.

Ice formation is also reduced by providing a colder surface near the detector. For example, in the system described in U.S. Pat. No. 5,274,237 to Gallagher et al. for a "Deicing Device for Cryogenically Cooled Radiation Detector," the heat generated by the detector circuitry maintains the detector a few degrees warmer than the collimator surface so that moisture sublimes from the detector surface onto the collimator surface. The heat generated by the circuitry provides a temperature difference of only about five degrees, which may not be adequate to maintain an ice-free surface on the detector. U.S. Pat. No. 4,931,650 to Lowe et al. for "X-ray Detectors" describes periodically heating the detector above its operating temperature while maintaining a heat sink at operating temperature. Periodically heating the detector above its operating temperature does not stop the build-up of ice during operation and requires periodic interruption of the system operation to remove the ice.

For greatest sensitivity, the detector should cover a large solid angle from the sample to collect as many of the emitted x-rays as possible. To increase the solid angle, the detector can provide a larger active surface area, or be placed closer to the sample. In a transmission electron microscope, the pole pieces and sample holder take up most of the space around the sample and it can be difficult to position X-ray detectors close to the sample to increase the solid angle. U.S. Pat. No. 4,910, 399 to Taira et al. teaches a configuration that puts a detector closer to the sample and allows the detector to subtend a larger solid angle. Another configuration is shown in Kotula et al., "Results from four-channel Si-drift detectors on an SEM: Conventional and annular geometries," *Microscopy and Microanalysis,* 14 Suppl 2, p. 116-17 (2008). Kotula et al. describe a four-segment detector, with each segment being kidney-shaped and having an active area of about 15 $mm^2$. The detector is positioned above the sample below the pole piece of an SEM, with the four segments distributed in a ring that is coaxial with the electron beam. This configuration is not normally possible in a high-resolution TEM.

SUMMARY OF THE INVENTION

An object of the invention, therefore, is to provide an x-ray detector having improved detection capabilities.

A preferred embodiment uses multiple detectors arranged in a ring within a specimen chamber to provide a large solid angle of collection. The detectors preferably include a shutter and a cold shield that reduce ice formation on the detector. By providing detectors surrounding the sample, a large solid angle is provided for improved detection and x-rays are detected regardless of the direction of sample tilt.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Figure 1:
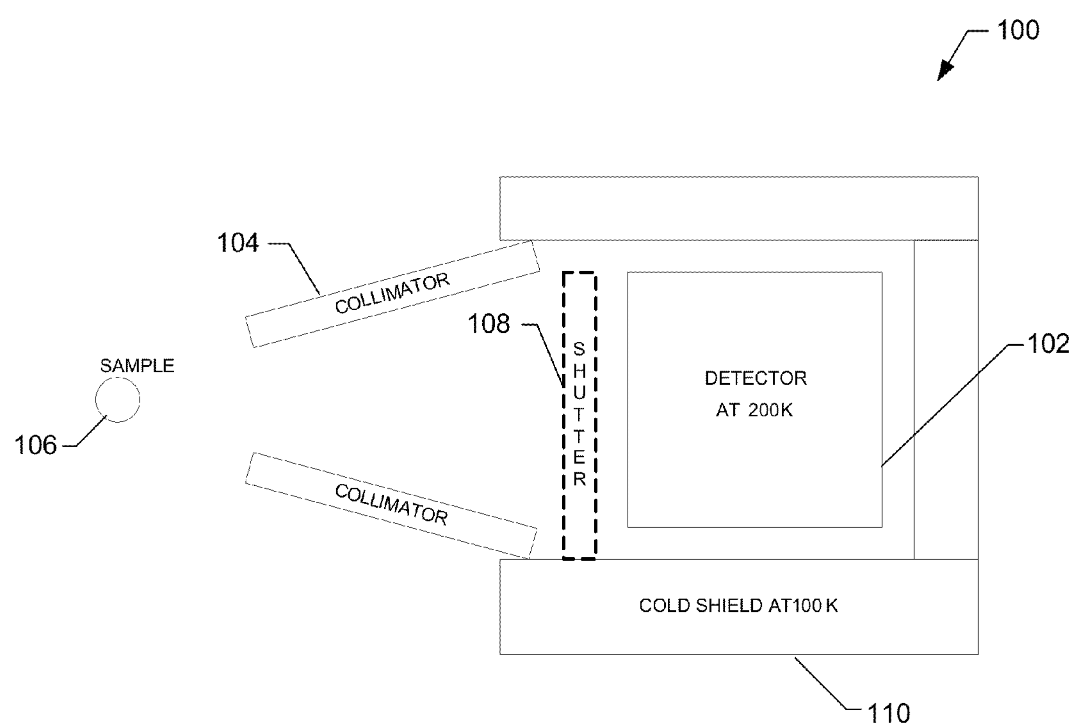
FIG. 1 shows schematically a preferred detector of the present invention.

A preferred embodiment uses multiple detector assemblies arranged in a ring within a specimen chamber to provide a large solid angle of collection. FIG. 1 shows schematically a preferred embodiment of one of the multiple detector assemblies 100. Each detector assembly 100 includes a SDD detector 102 having an active area of preferably greater than 10 $mm^2$, more preferably greater than 20 $mm^2$, and even more preferably about 30 $mm^2$. In some embodiments, each detector includes an active area of between 50 $mm^2$ and 100 $mm^2$. The detector of FIG. 1 includes a collimator 104 that prevents stray x-rays from entering the detector, ensuring that the signal from the detector corresponds to the x-rays emitted from a sample 106. A mechanical shutter 108, shown in the closed position, prevents electrons and low-energy x-rays from damaging the detector when it is not in use.

The SDD detector 102 is cooled to about 200 K using liquid nitrogen and is surrounded by a cold shield 110 maintained at about 100 K. In other embodiments, the detectors are maintained at temperatures of between about −60° C. and about −80° C. for optimum detector performance. However, it is possible to operate the SDD at higher temperatures, up to and including room temperature. Harmful background gases in an electron microscope are mostly water vapor and hydrocarbons, such as, for example, oils. Ice and hydrocarbons tend to condense onto the detectors, absorbing some incident x-rays and reducing the collection efficiency. Maintaining the detector cold shield at a temperature that is significantly colder than the detector and operating in an ultra high vacuum prevents the build-up of ice on the detector. The temperature difference between the detector and the cold shield is preferably greater than 10° C., more preferably greater than 25° C., even more preferably greater than 50° C., and most preferably equal to or greater than about 100° C. The shutter, which is maintained at about the same temperature as the cold shield, also protects the detector from ice formation. By reducing ice formation on the detector, a preferred detector does not require a window. Eliminating the window improves the detection efficiency for low-energy x-rays. Some embodiments, however, still use windows of a material, such as beryllium or thin polymer foils, which minimize x-ray absorption. Collimators 104 preferably are in thermal contact with cold shield 110 to provide additional cold shielding.

Figure 2:
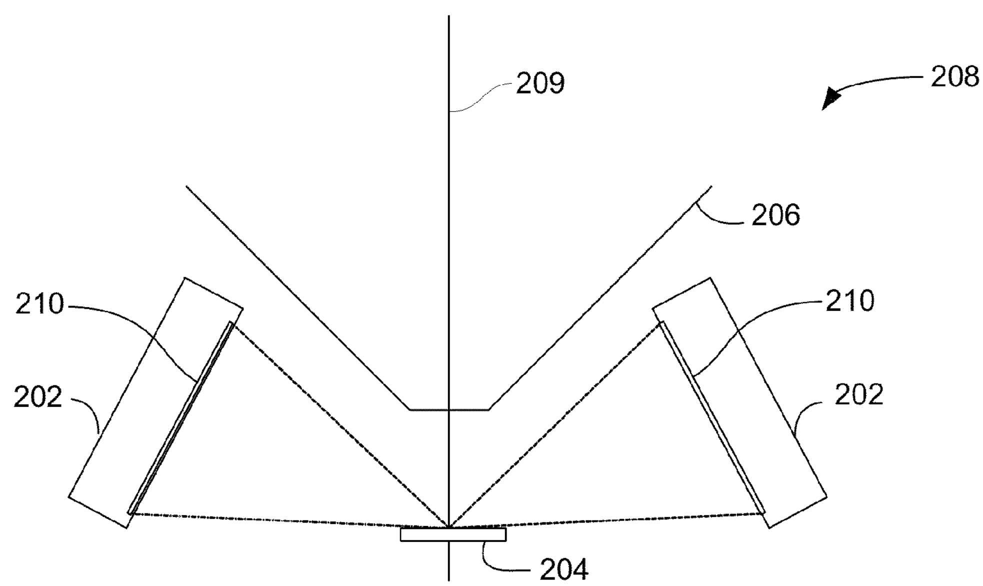
FIG. 2 shows the arrangement of detectors around a sample.

FIG. 2 shows a preferred arrangement of detectors 202 positioned around a sample 204 below, and thermally isolated from, an upper pole piece 206 of a TEM 208 having an optical axis 209. A preferred embodiment includes four detectors arranged around the sample, although only two are visible in FIG. 2. The two detectors 202 are positioned on opposite sides of the eucentric sample stage tilt axis, which is normal to the plane of the drawing. An active area 210 of each detector preferably subtends a solid angle of about ¼ steradian or greater to provide a total detector solid angle of about a steradian or greater. Each detector preferably detects x-rays at angles of less than 50 degrees from the sample surface, more preferably at angles of less than 35 degrees from the sample surface, and more preferably at angles between 5 and 35 degrees from the sample surface. The low take-off angle reduces damage from backscattered electrons, while maintaining bremsstrahlung radiation, which also gives rise to background in the spectra, but at a reasonably low level. The low take-off angle detectors also require no space between the pole pieces, thereby not requiring a degradation of the TEM or STEM resolution and sample tilt range. When the term "take-off angle" is used to describe a location or orientation of a detector, it is assumed that the sample surface is horizontal.

Figure 3:
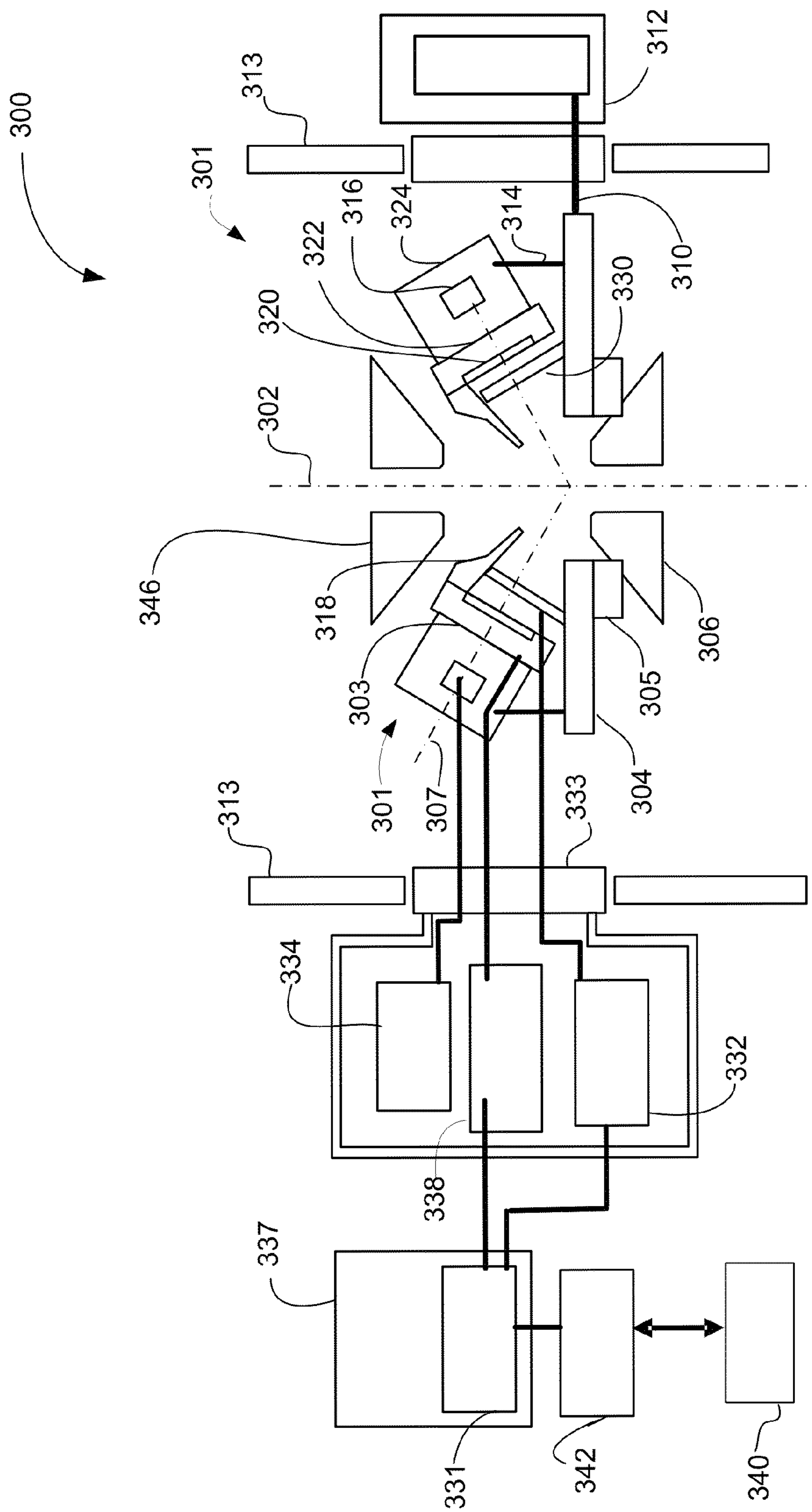
FIG. 3 shows the mechanical layout of a preferred detector embodiment.

FIG. 3 shows schematically a TEM 300 including four x-ray detectors assemblies 301 (only two shown) positioned around a TEM optical axis 302. Each x-ray detector assembly 301 includes an X-ray detector 303, which is preferably an SDD detector, which is known in the art. X-ray detector assemblies 301 are supported by a support ring 304 which is in turn supported by a lower pole piece 306 with a thermal insulator 305 thermally isolating support ring 304 from lower pole piece 306. The optical axis 307 of each detector assembly 301 preferably intersects the optical axis 305 of the TEM at the sample surface. Thermal conductor 310, preferably a copper braid or rod, connects support ring 304 with a cold source, such as a Dewar flask 312 of liquid nitrogen maintained outside of vacuum chamber walls 313. A support 314 provides support to each detector assembly 301 from support ring 304 and provides a resistive thermal path from support ring 304 to detectors 303, that is, support 314 provides a thermal path between support ring 304 and detector 303, but restricts the thermal flow. A resistive heater 316 maintains the temperature of each detector 303 significantly greater than the temperature of support ring 304. Detectors 303 are preferably maintained at a temperature difference of greater than 20° C., greater than 50° C., or approximately equal to or greater than 100° C., relative to support ring 304. A collimator is formed by an upper collimator 318 and a portion of support ring 304. The use of an SDD detector, which can operate efficiently at a temperature significantly higher than the optimum operating temperature for a Si(Li) detector, allows the detector to be operated at a temperature significantly above the temperature of liquid nitrogen. This facilitates the use of a single liquid nitrogen cold source to cool both the detector and a cold shield, while allowing the cold shield to be maintained at a much lower temperature than the detector, which improves protection of the detector from contamination by condensates.

Each detector 303 includes an active area 320 positioned on a ceramic substrate 322 supported by a metal base 324. Four shutters 330 protect the four detectors 303 from ice formation and from high energy electrons when closed. During operation, the shutters are moved to an open position to allow x-rays to reach the active area 320. The shutters are in thermal contact with support ring 304, which keeps them at about the same temperature as support ring 304 and at a temperature significantly lower than the temperature of detector 303. Support ring 304, shutters 330, and preferably upper collimator 318, function as a cold shield, causing moisture to sublime from the detector active area 320 onto the support ring 304, shutters 330, and collimator 318. The shutters are controlled by a shutter controller 331 through a shutter activator 332 which connects to the shutters through a mechanical linkage via a vacuum feed-through 333 from outside the vacuum chamber walls 313. In one embodiment, each shutter activator activates two shutters. TEM 300 is controlled by a user 340 through the TEM Personal computer 342.

A heater controller 334 controls the current to heater 316 to maintain a desired temperature of detector active area 320. A pre-amp 338 receive a signal from the detector 303. The signal is processed by a pulse processer 337 to determine the number of x-rays counted and the energy of each x-ray. Pulse processing techniques are well known in the EDS art.

Prior art detectors were typically attached to the vacuum chamber wall, more than 10 cm away from the sample, which made it difficult to keep the detectors aligned with the sample. When a detector is even 0.2 mm out of position, it is no longer "looking" at the point at which the x-rays are generated, and therefore picks up unwanted signals. In preferred embodiments of the present invention, the detector assembly is attached within the TEM lens assembly, preferably to the lower pole piece. Because the detector is typically cooled to cryogenic temperature, it would have been considered undesirable to attach the detector assembly to the pole pieces, because it could lead to thermal instability. Applicants have found, however, that insulation 305 between the detector assembly and the pole pieces reduces thermal instabilities. The detector can also be secured to or against an upper pole piece 346 to provide additional alignment and stability. Moreover, the electric field from the detector, particularly a windowless detector, affects the electrons in the primary beam. Applicants have found that any deflection in the primary electron beam is relatively small and that the improved accuracy of the detector positioning outweighs any disadvantages of the mounting. Mounting the detector assembly onto the lens provides improved mechanical accuracy relative to the specimen.

Figures 4A, 4B:
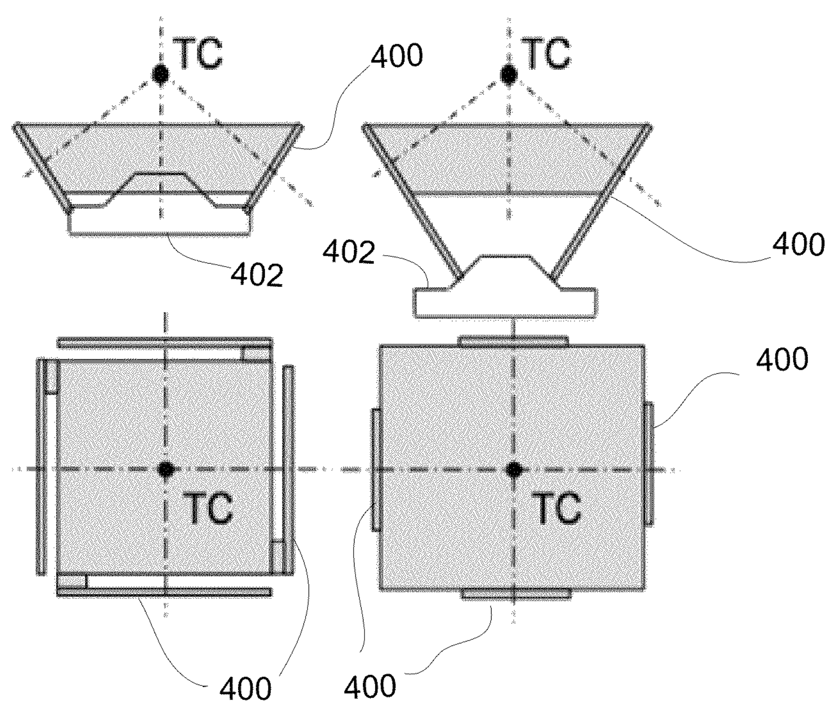
FIGS. 4A and 4B show structures for mounting the detectors in which the target point of the detectors remains relatively constant as the temperature changes.

FIGS. 4A and 4B show two designs for supporting a detector support ring 402 that in turn supports at least two individual detectors assemblies. Each design is shown in a front view and a top view. Both designs support the detector support ring using flexible elements 400, such as leaf springs, that are connected on the one end to the detector support ring and on the other end to a support, such as a portion of the lens. The detector support ring is preferably supported within the TEM lens, preferably on the lower pole piece (not shown). The flexible elements provide a floating thermal and vibration isolation platform on which to mount the detectors.

It is desirable that the detectors maintain their aim on the intersection of the optical axis and the sample surface as the detectors are cooled to operating temperature so that the detector can be aligned at room temperature and then stay aligned as it is cooled. In the design of FIG. 4A, the thermal center, that is, the point on the sample being analyzed, preferably does not move as the temperature of the detector changes. That is, the detectors are always 'looking' at approximately the same point: the intersection of the sample with the axis of the microscope as the temperature changes. The symmetry of the four leaf springs provides a slight rotation about the microscope axis as the assembly is cooled to operating temperature, as well as a radial contraction. The material of the leaf springs and the construction of components are selected to provide thermal coefficients of expansion that provide thermal stability such that the thermal center of the detectors on the microscope axis changes by less than 10 μm when the assembly is cooled from room temperature to cryogenic temperatures, such as to 100 K for the support ring. The thermal expansion coefficients of the different materials used to support the detector support are matched to achieve a net near-zero displacement of the thermal center. The thermal gradient in the flexible elements during operation is preferably linear, while the thermal gradient in the detector support ring is minimal. The mass and the dimensions of the leaf springs raise the resonance frequency of the mount to minimize vibration. While leaf springs are described to float the detector mount, other types of mounts can also be used.

In the design of FIG. 4A, a change in temperature causes expansion of the flexible elements, which causes a slight rotation about the point TC on the optical axis and a radial contraction. The rotation about the point TC is not detrimental since x-ray emission is isotropic in the azimuthal direction. In the design of FIG. 4B, a change in temperature causes translation parallel to the optical axis, which is less preferred.

The support ring may include an opening that accepts the upper pole piece of a TEM and a thermal isolation material thermally isolates the cold components from the upper pole piece. Openings in the ring support can be provided for inserting the sample, an aperture, or other devices. By mounting the support ring on the lower pole piece, the positioning of the x-ray detectors relative to the sample is maintained more accurately than the positioning of prior art detectors, which are mounted onto the walls of the vacuum chamber.

The invention allows three-dimensional X-ray tomography and depth determination of features in the specimen without requiring a series of images at different tilt angles. In the prior art, X-ray tomography was performed by obtaining a series of images at different sample tilts. The images at the different tilts were analyzed by a computer to determine the three dimensional structure of the sample region. Because the present invention provides multiple detectors, it is possible to use the difference in signal strengths between the detectors to determine the depth of a feature or the three dimensional distribution of materials.

Figure 5:
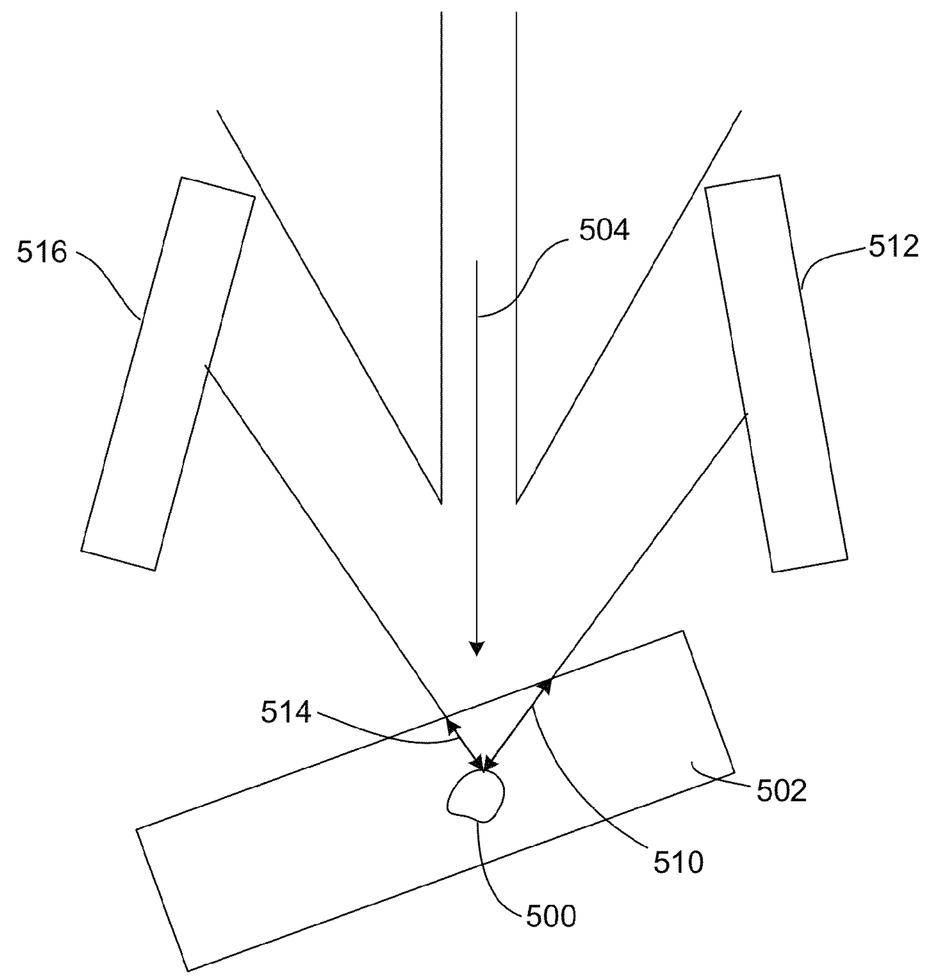
FIG. 5 shows how the difference in x-ray path length can be used in x-ray tomography without requiring a series of tilt images.

FIG. 5 shows a defect 500 in a sample 502 under an electron beam 604. X-rays emitted from the defect travel through the sample a distance 510 before reaching detector 512. X-rays emitted from the defect travel through the sample a distance 514 before reaching detector 516. The x-rays are attenuated as they travel through the sample, and so the x-ray signal at detector 512 will be different from the x-ray signal at detector 516. The X and Y coordinates of the point at which the x-rays are generated is known from the known position of the scanned image. The Z position of the point from which the x-rays are generated can then be determined from the differences in signal strength at the different detectors, based on the different path lengths through the sample material.

Another use of the multiple detectors is differential x-ray detection, i.e. subtracting the signal from the 4 detectors in some combinations like (A+B)−(C+D). This could be used to detect local differences in material properties or magnetic anisotropy, for example, in addition to the tomography application.

Conventional x-ray tomography is enhanced through the use of multiple detectors by increasing signal acquisition rates and/or by combining information from a tilt series with information from difference in signal intensity, as described with respect to FIG. 5, from the multiple detectors Embodiments of the invention substantially increase X-ray count rates compared to most prior art detectors. Unlike the prior art, in which the sample needs to be tilted toward the x-ray detector, embodiments of the invention allow detection at any tilt angle of the specimen under observation or at any stage rotation, because the detectors surround the sample. In some embodiments, the functionality of the cold trap and cooling for the detectors is combined in one liquid nitrogen Dewar, rather than the two Dewars normally required, thereby reducing the chance of adverse effects on the image resolution of the microscope. The multiple detectors and the large solid detection angle, preferably about one steradian or greater, allows X-ray mapping, which previously required more than 1 hour measurement time, to be performed in a few minutes.

The invention also leads to new possibilities for X-ray detection, such as 3D X-ray tomography and depth determination of features in the specimen. Here the independent directional detection of the X-rays received by the multiple detectors carry the information about the exact 3D position of the area on the sample emitting the X-rays.

While the embodiments described above describe the implementation of x-ray detectors for a transmission electron microscope, the invention is not limited to implementation in a TEM, but can be implemented in other instruments, such as scanning electron microscopes and scanning transmission electron microscopes.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable.

The drawings are intended to aid in understanding the present invention and, unless otherwise indicated, are not drawn to scale.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. An electron microscope, comprising:

a detector mounting structure; and at least two detectors supported by the detector mounting structure such that an optical axis of each of the at least two detectors intersects an optical axis of the electron microscope, wherein the detector mounting structure is configured to cause a translation of the at least two detectors parallel to the optical axis of the electron microscope in response to a change in temperature.

2. The electron microscope of claim 1, wherein the detector mounting structure comprises a detector support ring and flexible elements, a first end of each of the flexible elements being connected to the detector support ring.

3. The electron microscope of claim 2, wherein the flexible elements are arranged symmetrically about the optical axis of the electron microscope.

4. The electron microscope of claim 3, wherein the detector mounting structure comprises four flexible elements.

5. The electron microscope of claim 2, wherein the flexible elements comprise leaf springs.

6. The electron microscope of claim 2, further comprising a lens and wherein a second end of each of the flexible elements is connected to a portion of the lens.

7. The electron microscope of claim 1, wherein the electron microscope is a transmission electron microscope or a scanning electron microscope.

8. A mounting structure for x-ray detectors of an electron microscope, comprising:

a detector support ring configured to support at least two x-ray detector assemblies in an alignment during an analysis of a sample by an electron microscope wherein each of the at least two x-ray detectors is aimed at a point on the sample; and flexible elements, each of the flexible elements comprising a first end connected to the detector support ring, wherein a change in temperature causes expansion of the flexible elements.

9. The mounting structure of claim 8, wherein a second end of each of the flexible elements is adapted to be connected to a lens of the electron microscope.

10. The mounting structure of claim 9, wherein the expansion of the flexible elements causes the at least two x-ray detector assemblies to rotate about and contract radially toward a thermal center of the at least two x-ray detector assemblies when the flexible elements are connected to the lens of the electron microscope.

11. The mounting structure of claim 10, wherein the thermal center does not change in response to the change in temperature.

12. The mounting structure of claim 9, wherein the flexible elements are configured to be arranged symmetrically about an optical axis of the electron microscope when the flexible elements are connected to the lens.

13. The mounting structure of claim 12, wherein the mounting structure comprises four flexible elements.

14. The mounting structure of claim 8, wherein the flexible elements comprise leaf springs.

15. The mounting structure of claim 14, wherein materials of the leaf springs and a construction of the mounting structure provide thermal coefficients of expansion that provide thermal stability such that a thermal center of the detectors on an optical axis of the electron microscope changes by less than 10 μm when the detector support ring is cooled from room temperature to a cryogenic temperature greater than or equal to about 100 K.

16. The mounting structure of claim 8, wherein the flexible elements exhibit a linear thermal gradient and the detector support ring exhibits substantially no thermal gradient during an operation of the electron microscope.

17. The mounting structure of claim 8, wherein the change in temperature is a temperature change occurring during a cooling of the at least two x-ray detectors to an operating temperature of the electron microscope.

18. The mounting structure of claim 17, wherein the operating temperature is a cryogenic operating temperature of greater than 100 K.

19. A detector support for a transmission electron microscope comprising a detector support ring and flexible elements, wherein a first end of each of the flexible elements is connected to the support ring, and wherein the detector support ring and the flexible elements are configured to support at least two detectors in a circumferential arrangement around an optical axis of the transmission electron microscope such that:

an optical axis of each of the at least two detectors intersects the optical axis of the transmission electron microscope; and a target point of the at least two detectors is maintained relatively constant over a temperature change.

20. The detector support of claim 19, wherein a second end of each of the flexible elements is configured for connection to a lens of the electron microscope.

21. The detector support of claim 20, wherein the lens is a TEM lens comprising an upper pole piece, and wherein the detector support ring comprises a thermal isolation material configured to thermally isolate the at least two detectors from the upper pole piece.

* * * * *